United States Patent [19]

Bush

[11] 4,031,271
[45] June 21, 1977

[54] ALKALI-RESISTANT RADIATION CURABLE ENE-THIOL COMPOSITIONS

[75] Inventor: Richard Wayne Bush, Columbia, Md.

[73] Assignee: W. R. Grace & Co., New York, N.Y.

[22] Filed: Nov. 17, 1975

[21] Appl. No.: 632,326

[52] U.S. Cl. .................................. 427/43; 427/44; 427/273; 427/305; 96/35.1; 96/36.2; 96/115 R

[51] Int. Cl.² ........................................ B05D 3/06

[58] Field of Search ............... 427/43.44, 273, 305; 96/35.1, 36.2, 27 R, 115 R; 260/79, 609 R

[56] References Cited

UNITED STATES PATENTS

| | | | |
|---|---|---|---|
| 3,138,573 | 6/1964 | LeFave et al. | 260/874 |
| 3,278,496 | 10/1966 | LeFave et al. | 260/79 |
| 3,904,499 | 9/1975 | Morgan | 96/115 R |

Primary Examiner—John H. Newsome

Attorney, Agent, or Firm—Richard P. Plunkett; Kenneth E. Prince

[57] ABSTRACT

The invention is directed to alkali-resistant, radiation curable compositions comprising A. a polyene and B. a polythiol of the formula

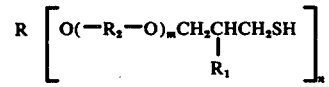

where R is an aliphatic hydrocarbon moiety containing 2–6 carbon atoms, $R_2$ is an alkylene group containing 2–6 carbon atoms, $R_1$ is hydrogen or —OH, $n$ is 2–6, and $m$ is 1–2.

A photosensitizer is added to the composition when curing is by U. V. radiation. The cured composition is operable as an additive plating resist in the manufacture of electronic circuitry.

6 Claims, No Drawings

ALKALI-RESISTANT RADIATION CURABLE ENE-THIOL COMPOSITIONS

This invention relates to radiation curable compositions and the cured products resulting therefrom being hydrolysis-resistant, particularly alkali hydrolysis-resistant. For purposes of brevity such resistance will hereinafter be referred to as alkali-resistant.

In the formation of electronic circuitry on insulated boards the use of photopolymers as a resist has become widespread. One such composition presently being used as a resist is that set out in U.S. Pat. No. 3,661,744 assigned to the same assignee. Therein liquid polyene-polythiol compositions containing a photosensitizer are photocured to form a resist on circuit boards. Although said compositions are operable in many of the conventional substractive circuit board manufacturing techniques, they are not employed in additive plating due to their poor alkali-resistance. That is, in additive plating, for example, of a copper circuit onto a circuit board by the electroless method, it is necessary that the resist withstand pH's in the range 10–14 since this is the range usually employed in the electroless copper bath used to plate copper onto the board.

Thus, one object of the instant invention is to provide an alkali-resistant composition which upon curing can act as a resist in an additive electroless plating process.

The above and other objects which will become apparent from a reading hereinafter are obtained from an alkali-resistant, radiation curable composition comprising A. a polyene component of the formula:

wherein $m$ is an integer of at least 2, wherein X is a member selected from the group consisting of:

(a) 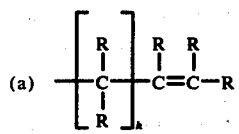

(b) 

(c) 

(d) 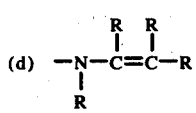

(e) 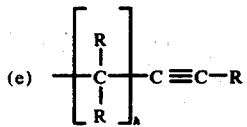

(f) 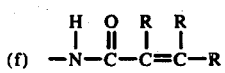

where $h$ is an integer from 1 to 9; R is a radical selected from the group consisting of hydrogen, fluorine, chlorine, furyl, thienyl, pyridyl, phenyl and substituted phenyl, benzyl and substituted benzyl, alkyl and substituted alkyl, alkoxy and substituted alkoxy, cycloalkyl and substituted cycloalkyl; said substituents on said substituted members selected from the group consisting of nitro, chloro, fluoro, acetoxy, acetamide, phenyl, benzyl, alkyl, alkoxy and cycloalkyl; said alkyl and alkoxy having from one to nine carbon atoms and said cycloalkyl having from three to eight carbon atoms; wherein [A] is free of reactive carbon-to-carbon unsaturation; free of highly water-sensitive members; and is a polyvalent chemically compatible member of the group consisting of carbonyl, ether, silane, silicate, phosphonate, phosphite, phosphate, alkyl and substituted alkyl, cycloalkyl and substituted cycloalkyl, aryl and substituted aryl, urethane and substituted urethane, urea and substituted urea, amine and substituted amine, amide and substituted amide, hydroxyl heterocyclic carbon containing radical, and mixtures thereof; said substituents on said members being defined above, said component having a molecular weight in the range from about 64 to 20,000; and a viscosity in the range from essentially 0 to 20 million centipoises at 70° C; and B. a polythiol of the formula

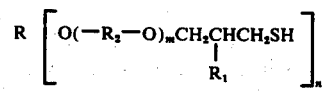

where R is an aliphatic hydrocarbon moiety containing 2–6 carbon atoms, $R_2$ is an alkylene group containing 2–6 carbon atoms, $R_1$ is hydrogen or —OH, $n$ is 2–6, and $m$ is 1–2.

The polythiols of the instant invention are commercially available and can be prepared in accord with the teaching set out in U.S. Pat. No. 3,258,495 and 3,278,496 and incorporated by reference herein.

Commercially available polythiols are usually esters of 3-mercaptopropionic or 2-mercaptoacetic acid with polyols such as trimethylolpropane or glycerol. These latter polythiols, however, due to their ester content, when cured with a polyene to form a resist coating, are unable to withstand the high alkaline environment present in an additive plating bath used to plate copper circuits onto circuit boards.

Generally stated, the present invention provides a curable composition which is alkali-resistant in its cured state which comprises 98 to 2 percent by weight of said composition of a polyene component and 2 to 98 percent by weight of said composition of the polythiol component. A photosensitizer is added when curing is by U. V. light.

The polyenes operable herein include, but are not limited to, those disclosed in U.S. Pat. Nos. 3,661,744 and 3,898,349 both incorporated herein by reference.

The polyene component may be represented by the formula:

wherein $m$ is an integer of at least 2, wherein X is a member selected from the group consisting of:

(a) 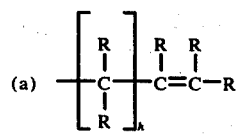

-continued (b) 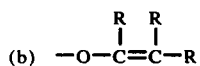

(c) 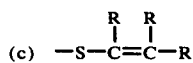

(d) 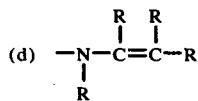

(e) 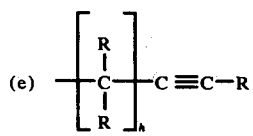

(f) 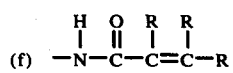

In the groups (a) to (f), $h$ is an integer from 1 to 9; R is a radical selected from the group consisting of hydrogen, fluorine, chlorine, furyl, thienyl, pyridyl, phenyl, and substituted phenyl, benzyl and substituted alkoxy, and cycloalkyl and substituted cycloalkyl. The substituents on the substituted members are selected from the group consisting of nitro, chloro, fluoro, acetoxy, acetamide, phenyl, benzyl, alkyl, alkoxy and cycloalkyl. Alkyl and alkoxy have from one to nine carbon atoms and cycloalkyl has from three to eight carbon atoms.

The members (a) to (f) are connected to [A] through divalent chemically compatible derivative members. The members (a) to (f) may be connected to [A] through a divalent chemically compatible derivative member of the group consisting of Si(R)$_2$, sulfone,

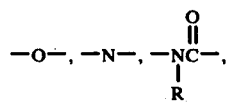

alkyl and substituted alkyl, cycloalkyl and substituted cycloalkyl, urethane and substituted urethane, urea and substituted urea, amide and substituted amide, amine and substituted amine, and aryl and substituted aryl. The alkyl members have from one to nine carbon atoms, the aryl members are either phenyl or naphthyl, and the cycloalkyl members have from three to eight carbon atoms with R and said members substituted being defined above.

The member [A] is polyvalent; free of reactive carbon-to-carbon unsaturation, free of highly water-sensitive members; free of hydrolysis-prone members, such as carboxylate ester; and consisting of atoms selected from the group consisting of carbon, oxygen, nitrogen, chlorine, bromine, fluorine, phosphorus, silicon and hydrogen. Said atoms are combined to form chemically compatible members of the group consisting of carbonyl, ether, silane, silicate, alkyl and substituted alkyl, cycloalkyl and substituted cycloalkyl, aryl and substituted aryl, urethane and substituted urethane, urea and substituted urea, amine and substituted amine, amide and substituted amide, hydroxyl, heterocyclic carbon containing radical, and mixtures thereof; said substituents on said members being defined above.

The polyene component has a molecular weight in the range from about 64 to 20,000 preferably about 200 to about 10,000; and a viscosity in the range from essentially 0 to 20 million centipoises at 70° C as measured by a Brookfield Viscometer.

The member [A] of the polyene composition may be formed primarily of alkyl radicals, phenyl and urethane derivatives, oxygenated radicals, and nitrogen substituted radicals. The member [A] may also be represented by the formula:

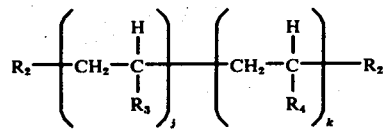

wherein j and k are integers greater than 1; R$_2$ is a member of the group consisting of hydrogen and alkyl having one to nine carbon atoms; R$_3$ is a member of the group consisting of hydrogen and saturated alkyl having one to nine carbon atoms; R$_4$ is a divalent derivative of the group consisting of phenyl, benzyl, alkyl, cycloalkyl, substituted phenyl, substituted benzyl, substituted alkyl and substituted cycloalkyl; with the terms alkyl, cycloalkyl and members substituted being defined above.

Representative formulas for polyenes operable in the present invention may be prepared as examplified below:

I. Poly (alkylene-ether) Polyol Reacted with Unsaturated Monoisocyanates Forming Polyurethane Polyenes and Related Polymers Trifunctional

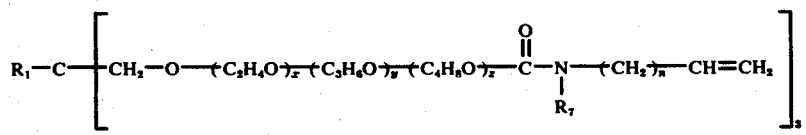

Tetrafunctional

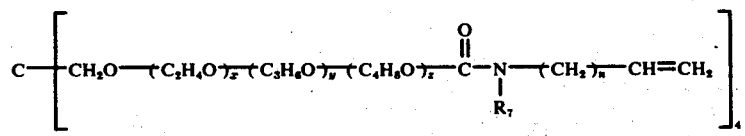

Tri-to-Hexafunctional

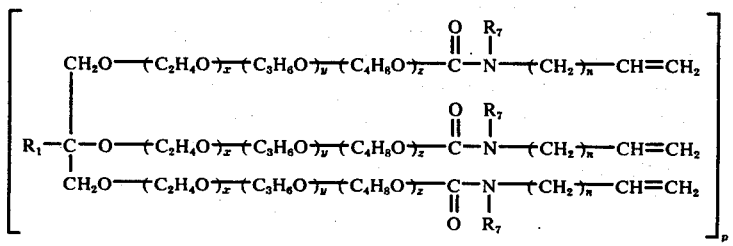

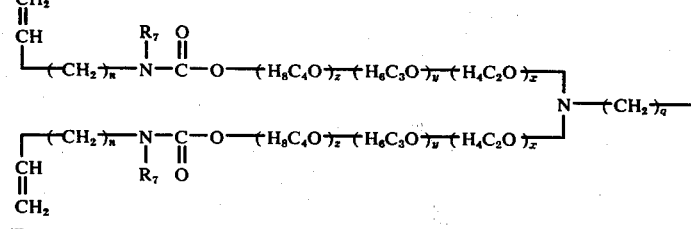

Interconnected-Modified Tetrafunctional

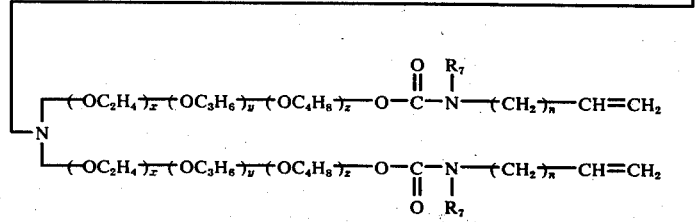

II. Poly (alkylene-ether)Polyol Reacted with Polyisocyanate and Unsaturated Monoalcohol Forming Polyurethane Polyenes and Related Polymers

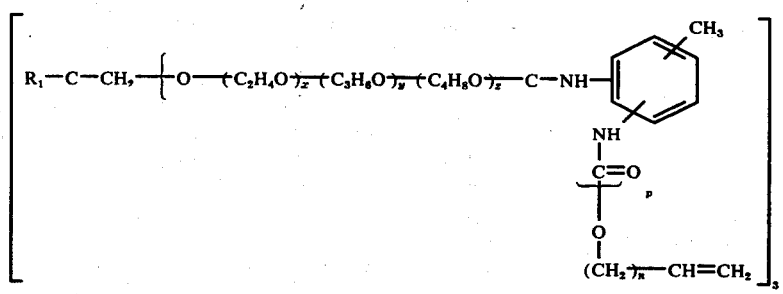

In the above formulas, the sum of $x + y + z$ in each chain segment is at least 1; $p$ is an integer of 1 or more; $q$ is at least 2; $n$ is at least 1; $R_1$ is selected from the group consisting of hydrogen, phenyl, benzyl, alkyl, cycloalkyl, and substituted phenyl; and $R_7$ is a member of the group consisting of $CH_2=CH-(CH_2)_n$, hydrogen, phenyl, cycloalkyl, and alkyl.

The class of polyenes of this invention derived from carbon-to-carbon unsaturated monoisocyanates may be characterized by extreme ease and versatility of manufacture when the liquid functionality desired in greater than about three. For example, consider an attempted synthesis of a polyhexene starting with an —OH terminated polyalkylene ether hexol such as "Niax" Hexol LS-490 (Union Carbide Corp.) having a molecular weight of approximately 700, and a viscosity of 18,720 cps at 20° C. An attempt to terminate this polymer with ene groups by reacting 1 mole of hexol with 6 moles of tolylene diisocyanate (mixed-2,4, 2-6-isomer product) and 6 moles of allyl alcohol proceeded nicely but resulted in a prematurely chain extended and crosslinked solid product rather than an intended liquid polyhexene. Using the monoisocyanate route, however, this premature chain extension may be avoided and the desired polyurethane-containing liquid polyhexene may be very easily prepared by a simple, one-step reaction of one mole of hexol with 6 moles of allyl isocyanate. This latter polyhexene has the added advantage of being cured using the teachings of this invention to a non-yellowing polythioether polyurethane product. Similarly, the unsaturated monoisocyanate technique may be used to prepare liquid polyenes from other analagous highly functional polyols such as cellulose, polyvinyl alcohol, partially hydrolyzed polyvinyl acetate, and the like, and highly functional polyamines such as tetraethylene pentamine, polyethyleneimine, and the like.

A general method of forming one type of polyene containing urethane groups is to react a polyol of the general formula $R_{11}(OH)_n$ wherein $R_{11}$ is a polyvalent organic moiety free from reactive carbon-to-carbon unsaturation and $n$ is at least 2 with a polyisocyanate of the general formula $R_{12}(NCO)_n$ wherein $R_{12}$ is a polyvalent organic moiety free from reactive carbon-to-carbon unsaturation and $n$ is at least 2 and a member of the group consisting of an ene-ol, yne-ol, ene-amine and yne-amine. The reaction is carried out in an inert moisture-free atmosphere (nitrogen blanket) at atmospheric pressure at a temperature in the range from 0° to about 120° C for a period of about 5 minutes to about 25 hours. In the case where an ene-ol or yne-ol is employed, the reaction is preferably a one step reaction. Where an ene-amine or yne-amine is used, the reaction is preferably a two step reaction wherein the polyol and the polyisocyanate are reacted together and thereafter preferably at room temperature, the ene-amine or yne-amine is added to the NCO terminated polymer formed. The group consisting of ene-ol, yne-ol, ene-amine and yne-amine are usually added to the reaction in an amount such that there is one carbon-to-carbon unsaturation in the group member per hydroxyl group in the polyol and said polyol and group member are added in combination in a stoichiometric amount necessary to react with the isocyanate groups in the polyisocyanate.

A second general method of forming a polyene containing urethane groups (or urea groups) is to react a polyol (or polyamine) with an ene-isocyanate or an yne-isocyanate to form the corresponding polyene. The general procedure and stoichiometry of this synthesis route is similar to that described for polyisocyanates in the preceding. In this instance, a polyol reacts with an ene-isocyanate to form the corresponding polyene. It is found, however, that products derived from this route, when cured in the presence of an active light source and a polythiol, may form relatively weak solid polythioether products. To obtain stronger cured products, it is desirable to provide polar functional groupings within the main chain backbone of the polymeric polyene. These polar functional groupings serve as connecting linkages between multiple repeating units in the main chain series, and serve as internal strength-reinforcing agents by virtue of their ability to create strong interchain attraction forces between molecules of polymer in the final cured composition.

A further group of polyenes which are operable in the present invention includes unsaturated polymers in which the double or triple bonds occur also within the main chain of molecules. These are derived primarily from standard diene monomers such as polyisoprene, butadiene, styrenebutadiene rubber, isobutylene-isoprene rubber, polychloroprene, styrene-butadiene-acrylonitrile rubber and the like unsaturated polyamides, and polyurethanes derived from monomers containing "reactive" unsaturation.

In forming the polyenes of the present invention, catalytic amounts of a catalyst may be employed to speed up the reaction. This is especially true in the case where an ene-ol is used to form the polyene. Such catalysts are well known to those in the art and include organometallic compounds such as stannous octoate, stannous oleate, dibutyl tin dilaurate, cobalt acetylacetonate, ferric acetylacetonate, lead naphthanate and dibutyl tin diacetate. The polyene/polythiol mole ratios are selected so as to provide a solid, self-supporting cured product under ambient conditions in the presence of actinic or high energy ionizing radiation.

The curing reaction can be initiated by either U. V. radiation or high energy ionizing radiation, i.e., radiation having an energy equivalent of 3.0 to 10 million electron volts. The U. V. radiation can be obtained from sunlight or special light sources which emit significant amounts of U. V. light having a wavelength in the range of about 2000 to 4100 Angstrom units. When U. V. radiation is used for the curing reaction, a dose of 0.0004 to 60 watts/centimeter$^2$ is usually employed.

When U. V. radiation is used for curling, a photosensitizer is added to the composition. Preferred photocuring rate accelerators or photosensitizers are the aldehyde and ketone carbonyl compounds having at least one aromatic nucleus attached directly to the

group. Various photosensitizers include, but are not limited to benzophenone, acetophenone, o-methoxybenzophenone, acenapthenequinone, methyl ethyl ketone, valerophenone, hexanophenone, γ-phenylbutyrophenone, p-morpholinopropiophenone, dibenzosuberone, 4-morpholinobenzophenone, 4'-morpholinodeoxybenzoin, p-diacetylbenzene, 4-aminobenzophenone, 4'-methoxyacetophenone, benzaldehyde, α-tetralone, 9-acetylphenanthrene, 2-aceytylphenanthrene, 10-thioxanthenone, 3-acetylphenanthrene, 3-acetylindole, 9-fluorenone, 1-indanone, 1,3,5-triacetylbenzene, thioxanthen-9-one, xanthene-9-one, 7-H-benz-[de]anthracen-7-one, 1-naphthaldehyde, 4,4'-bis(dimethylamino) benzophenone, fluorene-9-one, 1'-acetonaphthone, 2'-acetonaphthone, 2,3-butanedione, triphenylphosphine, tri-o-tolyphosphine, acetonaphthone, 2,3-butanedione, benz[a]anthracene 7,12 dione, etc. Another class of photosensitizers is the benzoin ethers, such as benzoin methyl ether, benzoin ethyl ether, benzoin isopropyl ether and benzoin isobutyl ether. Generally, these photosensitizers serve to give greatly reduced exposure times and thereby when used in conjunction with various forms of energetic radiation yield very rapid, commercially practical time cycles by the practice of the instant invention. The photosensitizers are usually added in an amount ranging from 0.0005 to 50% by weight of the polyene and polythiol.

The radiation curable compositions of the instant invention can also be cured by high energy ionizing irradiation. Preferred methods of the ionizing irradiation operation of the instant invention include treatment with high energy particle irradiation or gamma-rays or X-rays. Irradiation employing particles in the instant invention includes the use of positive ions, (e.g., protons, alpha particles and deuterons), electrons or neutrons. The charged particles may be accelerated to high speeds by means of various voltage gradient mechanisms such as a Van de Graaff generator, a cyclotron, a Cockroft Walton accelerator, a resonant cavity accelerator, a betatron, a G.E. resonant transformer, a synchrotron or the like. Furthermore, particle irradiation may also be supplied from radioactive isotopes or an atomic pile. Gamma rays or X-rays may be obtained from radioisotopes (e.g., cobalt 60) or by particle bombardment of suitable target material (e.g., high energy electrons on a gold metal target).

The dose rate for the irradiation operable to cure the coating in the instant invention is in the range 0.00001 to 1000 megarads/second.

The amount of ionizing radiation which is employed in curing the radiation curable material in the instant invention can vary between broad limits. Radiation dosages of less than a megarad up to 10 megarads or more for electrons are operable, preferably 0.02 to 5 megarads energy absorbed are employed. For gamma-rays or X-rays, radiation dosages in the range 0.0001 to 5.0 megarads energy absorbed are operable. The irradiation step is ordinarily performed under ambient temperature conditions but can be performed at temperatures ranging from below room temperature up to temperatures of 90° C.

The compositions to be radiation cured, i.e., converted to solid coatings, in accord with the present invention may, if desired, include such additives as antioxidants, inhibitors, activators, fillers, pigments, dyes, antistatic agents, flame-retardant agents, thickeners, thixotropic agents, surface-active agents, viscosity modifiers, plasticizers, and the like within the scope of this invention. Such additives generally are preblended with the polyene or polythiol prior to coating it on the substrate. The aforesaid additives may be present in quantities up to 500 parts or more per 100 parts radiation curable compositions by weight and preferably 0.0005 to 300 parts on the same basis. The type and concentration of the additives must be selected with care so that the final composition remains radiation curable under conditions of exposure.

For a commercially useful screen printable additive plating resist, desirable additives include thickening agents, thixotropes, leveling agents, colorants and reodorants.

The curable polymer compositions of the instant invention prior to curing can be pumped, poured, brushed, sprayed, doctored, rolled, trowelled, dipped-coated, extruded or cast onto vertical or horizontal flat surfaces in a uniform fashion. Following such application curing in place to an insoluble solid can be made to occur very rapidly. The compositions can be applied to various substrates and adhere well to glass, wood, metals, concrete, certain plastics, paints, enamels, fabrics, paper, paper board, porcelain, ceramics, brick, cinder block, plaster and vinyl floor tile.

When used as a resist in additive plating, the cured composition usually has a thickness in the range 0.5–2.5 mils. However, for other general uses requiring alkali resistance, coatings having thicknesses ranging from 0.2 to 250 mils are obtainable.

The polythioether-forming components and compositions of the instant invention can, prior to curing, be admixed with or blended with other monomeric and polymeric materials such as thermoplastic resins, elastomers or thermosetting resin monomeric or polymeric compositions. The resulting blend can be subjected to conditions for curing or co-curing of the various components of the blend to give cured products having unusual physical properties. Examples of the classes of the materials which can be admixed, blended or co-cured with the polythioether-forming compositions of the instant invention are illustrated by, but not limited to, the following: epoxy resins, phenolic resins, polysulfide resins, and elastomers, polyurethane resins and elastomers, polyamide resins, polyvinylchloride resins, amphorous or crystalline polyolefins, polyacrylonitrile polymers, silicon polymers, urea-formaldehyde resins, polyether resins and elastomers and the like.

The solid cured polythioether polymer products resulting from the instant invention have many and varied uses. Examples of some uses include but are not limited to adhesives; caulks; elastomeric sealants, coatings, such as wire coatings, cover resists for electrical circuits, photoresists and the and coatings, mastics; glazing compounds; fiberglass reinforced composites; sizing or surface finishing agents, filleting compounds; cured in place gasketing compounds; rocket fuel binders; foamable thermosetting resins or elastomers; molded articles such as gaskets, diaphragms, balloons, automobile tires, etc.

The molecular weight of the polyenes of the present invention may be measured by various conventional methods including solution viscosity, osmotic pressure and gel permeation chromatography. Additionally, the molecular weight may be calculated from the known molecular weight of the reactants.

The viscosity of the polyenes and polythiols may be measured on a Brookfield Viscometer at 30° or 70° C in accord with the instructions therefor.

The components to be cured may be prepared as either single-packaged or multi-packaged polymer systems which may be cured to solid polythioether elastomers without liberating gaseous by-products which cause bubbles and voids in the vulcanizate. Thus, there is provided curable polymer systems composed of polyenes and polythiols in which the components individually are storage stable and which are not sensitive to or deteriorated by traces of moisture or oxygen-containing gas such as may be encountered during normal storage or handling procedures. Solid resinous or elastomeric products may be prepared in a system in which the rate of curing may be inhibited or retarded by the use of chemical inhibitors, antioxidants, and the like. Conventional curing inhibitors or retarders which may be used in order to stabilize the components or curable compositions so as to prevent premature onset of curing may include certain acids and bases; hydroquinone; p-tert-butyl catechol; 2,6-di-tert-butyl-4-methylphenol; phenothiazine; N-phenyl-2-naphthylamine; pyrogallol; octadecyl-$\beta$-(4-hydroxy-3,5-di-t-butyl phenyl)-propionate; and the like.

The following examples will aid to explain but specifically not limit the instant invention. Unless otherwise noted, all parts and percentages are by weight.

EXAMPLE 1

1 gram-mole of a commercially available 80–20 percent isomer mixture of tolylene-2,4-diisocyanate and tolylene-2,6-diisocyanate, respectively, was charged to a resin kettle equipped with a condenser, stirrer, thermometer, and gas inlet and outlet. 2 gram-moles of the diallyl ether of trimethylolpropane was slowly added to the kettle. After the addition was complete, 0.5 grams of dibutyl tin dilaurate as a catalyst was added to the kettle and the reaction was continued for 30 minutes at 70° C under nitrogen. The thus formed allyl terminated liquid prepolymer of the formula

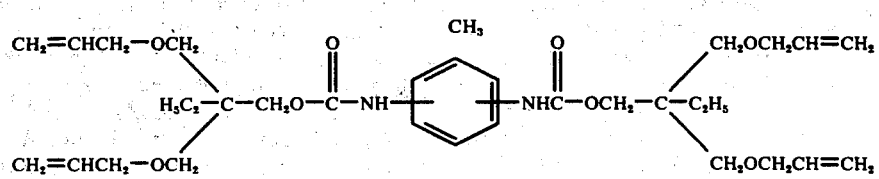

will hereinafter be referred to as Prepolymer A.

EXAMPLE 2

To a 1000 ml. glass resin kettle equipped with stirrer was charged 300 g of commercially available isophorone diisocyanate (9.0 meq NCO/g) and 0.3 g of stannous octoate catalyst. 297 g of commercially available trimethylolpropane diallyl ether (4.54 meq OH/g) was added slowly to the reactor while maintaining the temperature at 60° C. The reaction was continued until the isocyanate content was approximately 2.10 milliequivalents per gram. 138 g of commercially available 1,3-bis-(2-hydroxyethyl)-5,5-dimethylhydantoin (8.92 meq OH/g) was added over a 1 hour period while raising the temperature to 95° C. The reaction was continued at 95° C until NCO analyzed zero. The resultant product contained 3.78 mmoles of unsaturation per gram, vs. theory of 3.66 for the following structure:

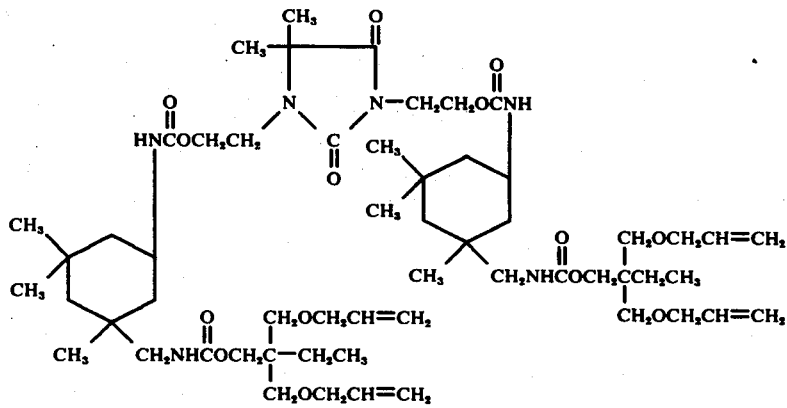

This product will hereinafter be referred to as Prepolymer B.

EXAMPLE 3

To a 500 ml. four neck resin kettle equipped with stirrer, gas inlet tube and thermometer was charged 123 g of commercially available trimethylolpropane mono-allyl ether and 74.5 g of commercially available trimethylolpropane diallyl ether. Stirring was commenced and 0.3 g of stannous octoate catalyst and 150 g of a commercially available 80–20 percent isomer mixture of tolylene-2,4-diisocyanate and tolylene-2,6-diisocyanate, respectively, was added to the kettle. The reaction was continued with stirring under nitrogen. The reaction exothermed to 100° C and was held at this temperature until the infrared spectrum showed no absorption for free isocyanate. About 3 hours reaction time was required. The resultant product of the formula

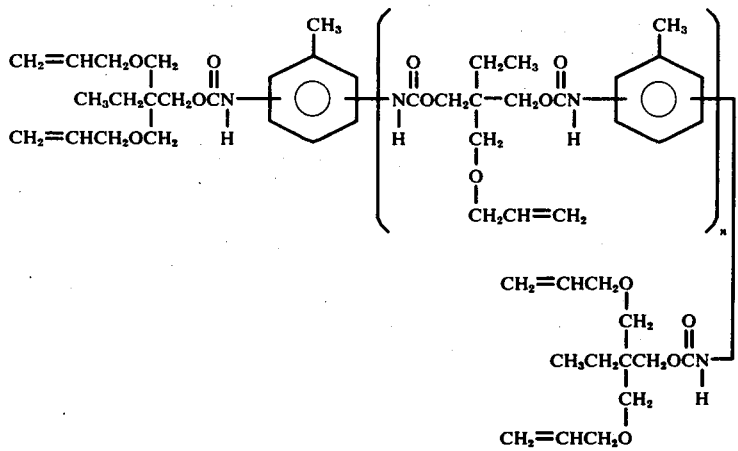

where the average value of $n = 4$ will hereinafter be referred to as Prepolymer C.

The following examples show the alkali resistance of the cured compositions of the instant invention.

EXAMPLE 4

35.84 grams of Prepolymer A from Example 1 along with 64.16 grams of a polythiol terminated polyoxyalkylene polyol commercially available under the tradename "DION" POLYMERCAPTAN DPM 3-800LC from Diamond Shamrock Chemical Co., 1.0 gram of benzophenone and as stabilizers 0.1 gram of pyrogallol and 0.02 gram of phosphorous acid were mixed until homogeneous and then coated to a thickness of about 1 mil on a 15 mil thick epoxy-fiberglass laminated board. The coated surface was exposed to U. V. light from two 25 inch 200 watt per inch medium pressure mercury vapor lamps situated approximately 3 inches from the surface of the coating in a Colight UVC-24 conveyerized curing system operated at a speed of 10 ft per minute. A hard coating resulted. The thus coated board was immersed in 1M sodium hydroxide at 70° C for 24 hours. On removing the coated board from the bath, no sign of attack of the coating was noted,

EXAMPLE 5

Example 4 was repeated except that 1.0 grams of benzoin isopropyl ether was substituted for 1.0 gram of benzophenone. The coating was not attacked in the NaOH immersion test.

EXAMPLE 6

A homogeneous mixture was made up of 34.19 grams of Prepolymer A from Example 1, 65.81 grams of a polythiol terminated polyoxyalkylene polyol commercially available under the tradename "DION" DPM 5-1300 from Diamond Shamrock Chemical Co., 1.0 gram of benzoin isopropyl ether, 0.1 gram of pyrogallol and 0.02 gram of phosphorous acid. The mixture was coated to a thickness of about 1 mil on a 15 mil thick epoxy-fiberglass laminated board and exposed to U. V. light from two 25 inch 200 watt/inch medium pressure mercury vapor lamps situated approximately 3 inches from the surface of the coating in a Colight UVC-24 conveyerized curing system operated at 10 ft per minute. A hard coating resulted. The thus coated board was immersed in 1M sodium hydroxide at 70° C for 24 hours. On removal from the sodium hydroxide, no sign of attack on the coating was noted.

EXAMPLE 7

A homogeneous mixture was made of 50.81 grams of Prepolymer B from Example 2, 49.19 grams of a polythiol terminated polyoxyalkylene polyol commercially available under the tradename "DION" POLYMERCAPTAN DPM 3-800LC from Diamond Shamrock Chemical Co., 1.0 gram of benzoin isopropyl ether, 0.1 gram of pyrogallol and 0.02 gram of phosphoruous acid. The mixture was coated and cured as in Example 4. The board with the cured coating thereon was immersed in 1M sodium hydroxide at 70° C for 24 hours. On removal from the sodium hydroxide, no attack of the coating was noted.

EXAMPLE 8

A homogeneous mixture of 48.45 grams of Prepolymer C from Example 3, 51.55 grams of a polythiol terminated polyoxyalkylene polyol commercially available under the tradename "DION" POLYMERCAPTAN DPM 3-800LC from Diamond Shamrock Chemical Co., 1.0 gram of benzoin isopropyl ether, 0.1 gram of pyrogallol and 0.02 gram of phosphorous acid was made up. The mixture was coated and cured as in Example 4. The thus coated board was immersed in 1M sodium hydroxide at 70° C for 24 hours. On removal from the sodium hydroxide bath, no attack of the coating was noted.

The following examples illustrate the analogous formulations made with commercially available ester-containing thiols are attacked in the NaOH immersion test.

EXAMPLE 9

A homogeneous mixture of 51.44 grams of Prepolymer A from Example 1, 48.56 grams of trimethylolpropane tris (β-mercaptopropionate) commercially available from Cincinnati Millicron under the tradename "P-33", 1.0 gram of benzoin isopropyl ether, 0.1 gram of pyrogallol and 0.02 gram of phosphorous acid was made up. The thus formed admixture was coated to a thickness of about 1 mil on a 15 mil thick epoxy-fiberglass laminated board and exposed to U. V. light from two 25 inch 200 watt/inch medium pressure mercury vapor lamps approximately 3 inches from the surface of the coating in a Colight UVC-24 conveyerized curing system operated at a speed of 10 ft per minute. A hard coating resulted. The thus coated board was immersed in 1M sodium hydroxide at 70° C for 24 hours. On removing the board from the sodium hydroxide bath, it was noted that the coating was completely removed therefrom.

EXAMPLE 10

A homogeneous mixture of 54.91 grams of Prepolymer A from Example 1, 45.09 grams of pentaerythritol tetrakis (β-mercaptopropionate) commercially available from Cincinnati Millicron under the tradename "Q-43", 1.0 gram of benzoin isopropyl ether, 0.1 gram of pyrogallol and 0.02 gram of phosphorous acid was made up. The admixture was then coated and cured as in Example 9. On removing the board after 24 hours from the 1M sodium hydroxide bath maintained at 70° C, it was noted that the coating was completely removed from the epoxy-fiberglass laminated board.

EXAMPLE 11

A homogeneous mixture of 69.25 grams of Prepolymer B from Example 2, 30.75 grams of pentaerythritol tetrakis (β-mercaptopropionate) commercially available from Cincinnati Millicron under the tradename "Q-43", 1.0 gram of benzoin isopropyl ether, 0.1 gram of pyrogallol and 0.02 gram of phosphorous acid was made up. The admixture was coated and cured as in Example 9. On removing the board after 24 hours from the 1M sodium hydroxide bath maintained at 70° C, it was noted that the coating was largely removed therefrom.

Resistance to Copper Sulfate Plating Solution

EXAMPLE 12

An electroless copper bath was prepared according to Example 1 of U.S. Pat. No. 3,095,309 consisting of 7.5 grams of copper sulfate pentahydrate, 15.0 grams of ethylenediamine tetraacetic acid tetrasodium salt dihydrate, 20 grams of sodium hydroxide, 0.5 gram of sodium cyanide, 40 ml of 40% formaldehyde and distilled water to make 1000 ml. Other typical electroless metal plating baths, as well as conventional sensitizing and activating solutions utilized in additive circuit processes, are disclosed in U.S. Pat. Nos. 3,546,009 and 3,573,973. A specimen of 60 mil thick epoxy fiberglass coated circuit board coated with the composition and cured by the procedure of Example 4 was immersed in the bath at 70° C for 24 hours and showed no attack.

EXAMPLE 13

Example 12 was repeated except that the cured coating was the composition of Example 7. The cured coating showed no attack.

EXAMPLE 14

Example 12 was repeated except that the cured coating was the composition of Example 8. The cured coating showed no attack.

Plating

EXAMPLE 15

A 60 mil epoxy-fiberglass circuit board was treated with a conventional SnCl$_2$ sensitizing solution followed by a conventional dilute palladium chloride seeding solution to promote adhesion of copper in the plating step. The board was coated through a screen containing the desired circuit image and cured using the composition and curing procedure of Example 4. The board was immersed in the electroless copper bath of Example 12 at 70° C for 24 hours. At the end of this time, the board contained a shiny deposit of tightly adhered copper in the areas not protected by the cured resist. The resist was unaffected by the bath and contained no evidence of spurious copper plating.

EXAMPLE 16

Example 15 was repeated except that the composition of Example 7 was substituted for the curable composition of Example 4. The results were the same as in Example 15.

EXAMPLE 17

EXAMPLE 15 was repeated except that the composition of Example 8 was substituted for the composition of Example 4. The results were the same as in Example 15.

EXAMPLE 18

A homogeneous mixture was made of 34.54 grams of prepoly Prepolymer A from Example 1. 64.46 grams of a polythiol terminated polyoxyalkylene polyol commercially available under the tradename DION DPM 3-700 from Diamond Shamrock Chemical Co. and containing no free hydroxyl groups, 25 grams of dispersion grade polyvinyl chloride sold under the tradename GEON 130 × 24 by B. F. Goodrich Co., 1.25 gram of benzoin isopropyl ether, 0.1 gram of pyrogallol, 0.02 gram of phosphorous acid, 0.25 gram of ethylene glycol and 3 grams of fumed silica sold under the tradename Cab-O-Sil M-5 by the Cabot Corporation. The mixture was coated and cured as in Example 4. The thus coated board was immersed in 1M solution hydroxide at 70° C for 24 hours. On removal from the sodium hydroxide bath, no attack of the coating was noted. Similarly the coated board was immersed in the electroless copper bath of Example 12 at 70° C for 24 hours. Again, no attack occurred.

We claim:

1. A composition capable of forming a solid, cured, alkali-resistant polythioether on exposure to radiation which comprises admixing A. an ester-free, water insoluble polyene component of the formula:

[A]-(X)$_m$ wherein $m$ is an integer of at least 2, wherein X is a member selected from the group consisting of:

(a) 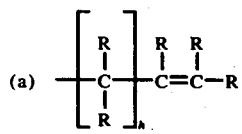

(b) 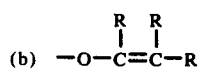

(c) 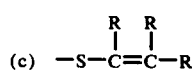

(d) 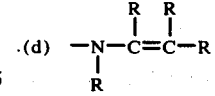

(e) 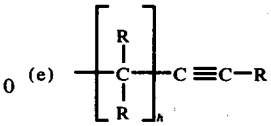

(f) 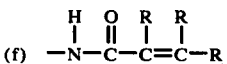

where $h$ is an integer from 1 to 9; R is a radical selected from the group consisting of hydrogen, fluorine, chlorine, furyl, thienyl, pyridyl, phenyl and substituted phenyl, benzyl and substituted benzyl, alkyl and substituted alkyl, alkoxy and substituted alkoxy, cycloalkyl and substituted cycloalkyl; said substituents on said substituted members selected from the group consisting of nitro, chloro, fluoro, acetoxy, acetamide, phenyl, benzyl, alkyl, alkoxy and cycloalkyl; said alkyl and alkoxy having from one to nine carbon atoms and said cycloalkyl having from three to eight carbon atoms; wherein [A] is free of reactive carbon-to-carbon unsaturation; and is a polyvalent chemically compatible member of the group consisting of carbonyl, ether, silane, silicate, phosphonate, phosphite, phosphate, alkyl and substituted alkyl, cycloalkyl and substituted cycloalkyl, aryl and substituted aryl, urethane and substituted urethane, urea and substituted urea, amine and substituted amine, amide and substituted amide, heterocyclic carbon containing radical, and mixtures thereof; said substituents on said members being defined above, said component having a molecular weight in the range from about 64 to 20,000; and a viscosity in the range from essentially 0 to 20 million centipoises at 70° C; and B. polythiol of the formula

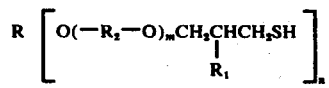

where R is an aliphatic hydrocarbon moiety containing 2–6 carbon atoms, $R_2$ is an alkylene group containing 2–6 carbon atoms, $R_1$ is hydrogen or —OH, $n$ is 2–6, and $m$ is 1–2.

2. A process for forming a copper pattern on a substrate suitably activated for electroless plating which comprises applying to the substrate in the non-pattern area, an alkali-resistant, radiation-curable composition comprising A. an ester-free, water insoluble polyene component of the formula:

[A]-(X)$_m$ wherein $m$ is an integer of at least 2, wherein X is a member selected from the group consisting of:

(a) 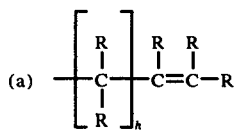

(b) 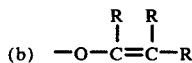

(c) 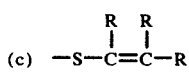

(d) 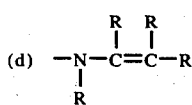

(e) 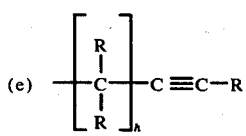

(f) 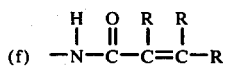

where $h$ is an integer from 1 to 9; R is a radical selected from the group consisting of hydrogen, fluorine, chlorine, furyl, thienyl, pyridyl, phenyl and substituted phenyl, benzyl and substituted benzyl, alkyl and substituted alkyl, alkoxy and substituted alkoxy, cycloalkyl and substituted cycloalkyl; said substituents on said substituted members selected from the group consisting of nitro, chloro, fluoro, acetoxy, acetamide, phenyl, benzyl, alkyl, alkoxy and cycloalkyl; said alkyl and alkoxy having from one to nine carbon atoms and said cycloalkyl having from three to eight carbon atoms; wherein [A] is free of reactive carbon-to-carbon unsaturation; free of highly water-sensitive members; and is a polyvalent chemically compatible member of the group consisting of carbonyl, ether, silane, silicate, phosphonate, phosphite, phosphate, alkyl and substituted alkyl, cycloalkyl and substituted cycloalkyl, aryl and substituted aryl, urethane and substituted urethane, urea and substituted urea, amine and substituted amine, amide and substituted amide, heterocyclic carbon containing radical, and mixtures thereof; said substituents on said members being defined above, said component having a molecular weight in the range from about 64 to 20,000; and a viscosity in the range from essentially 0 to 20 million centipoises at 70° C;

B. a polythiol of the formula

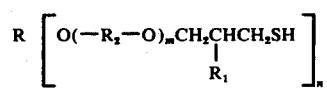

where R is an aliphatic hydrocarbon moiety containing 2–6 carbon atoms, $R_2$ is an alkylene group containing 2–6 carbon atoms, $R_1$ is hydrogen or —OH, $n$ is 2–6, and $m$ is 1–2, and C. a photosensitizer, exposing the composition to U.V. radiation for a time sufficient to form a cured polythioether coating in the non-pattern area and thereafter immersing the thus coated substrate in an alkaline aqueous copper-containing bath for a time sufficient to plate copper on the uncoated portion of the activated substrate.

3. The process according to claim 2 wherein the radiation is U.V. radiation and a photosensitizer is added to the mixture.

4. A process for forming a solid, cured, alkali-resistant polythioether which comprises admixing A. an ester-free, water insoluble polyene component of the formula:

wherein m is an integer of at least 2, wherein X is a member selected from the group consisting of:

(a) 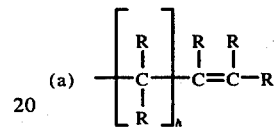

(b) 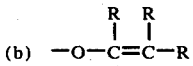

(c) 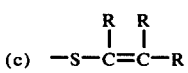

(d) 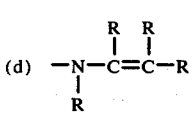

(e) 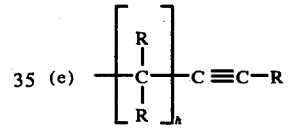

(f) 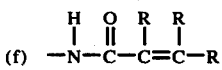

where $h$ is an integer from 1 to 9; R is a radical selected from the group consisting of hydrogen, fluorine, chlorine, furyl, thienyl, pyridyl, phenyl and substituted phenyl, benzyl and substituted benzyl, alkyl and substituted alkyl, alkoxy and substituted alkoxy, cycloalkyl and substituted cycloalkyl said substituents on said substituted members selected from the group consisting of nitro, chloro, fluoro, acetoxy, acetamide, phenyl, benzyl, alkyl, alkoxy and cycloalkyl; said alkyl and alkoxy having from one to nine carbon atoms and said cycloalkyl having from three to eight carbon atoms; wherein [A] is free of reactive carbon-to-carbon unsaturation; free of highly water-sensitive members; and is a polyvalent chemically compatible member of the group consisting of carbonyl, ether, silane, silicate, phosphonate, phosphite, phosphate, alkyl and substituted alkyl, cycloalkyl and substituted cycloalkyl, aryl and substituted aryl, urethane and substituted urethane, urea and substituted urea, amine and substituted amine, amide and substituted amide, heterocyclic carbon containing radical, and mixtures thereof; said substituents on said members being defined above, said component having a molecular weight in the range from about 64 to 20,000; and a viscosity in the range from essentially 0 to 20 million centipoises at 70° C; and B. a polythiol of the formula

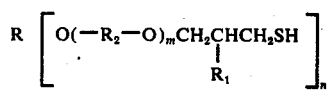

where R is an aliphatic hydrocarbon moiety containing 2–6 carbon atoms, $R_2$ is an alkylene group containing 2–6 carbon atoms, $R_1$ is hydrogen or —OH, $n$ is 2–6, and $m$ is 1–2 and thereafter exposing the mixture to radiation having an energy equivalent of 3.0 to 10 within electron volts.

5. The composition according to claim 1 containing in addition a photosensitizer.

6. A process for forming a copper pattern on a substrate suitably activated for electroless plating which comprises applying to the substrate in the non-pattern area an alkali-resistant, radiation-curable composition comprising A. an ester-free, water insoluble polyene component of the formula:

wherein $m$ is an integer of at least 2, wherein X is a member selected from the group consisting of:

(a) 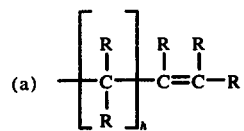

(b) 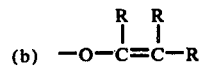

(c) 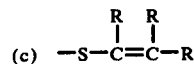

(d) 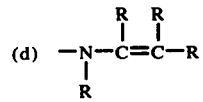

(e) 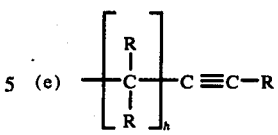

(f) 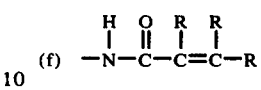

where $h$ is an integer from 1 to 9; R is a radical selected from the group consisting of hydrogen, fluorine, chlorine, furyl, thienyl, pyridyl, phenyl and substituted phenyl, benzyl and substituted benzyl, alkyl and substituted alkyl, alkoxy and substituted alkoxy, cycloalkyl and substituted cycloalkyl; said substituents on said substituted members selected from the group consisting of nitro, chloro, fluoro, acetoxy, acetamide, phenyl, benzyl, alkyl, alkoxy and cycloalkyl; said alkyl and alkoxy having from one to nine carbon atoms and said cycloalkyl having from three to eight carbon atoms; wherein [A] is free of reactive carbon-to-carbon unsaturation; free of highly water-sensitive members; and is a polyvalent chemically compatible member of the group consisting of carbonyl, ether, silane, silicate, phosphonate, phosphite, phosphate, alkyl and substituted alkyl, cycloalkyl and substituted cycloalkyl, aryl and substituted aryl, urethane and substituted urethane, urea and substituted urea, amine and substituted amine, amide and substituted amide, heterocyclic carbon containing radical, and mixtures thereof; said substituents on said members being defined above, said component having a molecular weight in the range from about 64 to 20,000; and a viscosity in the range from essentially 0 to 20 million centipoises at 70° C; and B. a polythiol of the formula

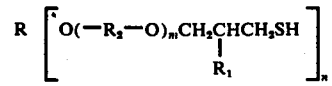

where R is an aliphatic hydrocarbon moiety containing 2–6 carbon atoms, $R_2$ is an alkylene group containing 2–6 carbon atoms, $R_1$ is hydrogen or —OH, $n$ is 2–6, and $m$ is 1–2.

* * * * *

UNITED STATES PATENT AND TRADEMARK OFFICE
CERTIFICATE OF CORRECTION

PATENT NO. : 4,031,271
DATED : June 21, 1977
INVENTOR(S) : Richard W. Bush

It is certified that error appears in the above-identified patent and that said Letters Patent are hereby corrected as shown below:

In column 17, line 39; column 18, line 54; column 20, line 24; delete "free of highly water-sensitive members".

In column 19, line 14; delete the word "within" and add the word --million--.

In column 20, line 49; add --exposing the composition to high energy ionizing radiation for a time sufficient to form a cured polythioether coating in the non-pattern area and thereafter immersing the thus coated substrate in an alkaline aqueous copper-containing bath for a time sufficient to plate copper on the uncoated portion of the activated substrate.--

Signed and Sealed this

Thirtieth Day of May 1978

[SEAL]

Attest:

RUTH C. MASON
Attesting Officer

LUTRELLE F. PARKER
Acting Commissioner of Patents and Trademarks